(12) United States Patent
Bastian

(10) Patent No.: US 6,586,585 B1
(45) Date of Patent: Jul. 1, 2003

(54) METHOD FOR THE SIZE REDUCTION OF HIGH-MOLECULAR STRUCTURES

(75) Inventor: Helge Bastian, Mettmann (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 08/669,432

(22) PCT Filed: Jan. 5, 1996

(86) PCT No.: PCT/EP95/00037

§ 371 (c)(1),
(2), (4) Date: Sep. 9, 1996

(87) PCT Pub. No.: WO95/18851

PCT Pub. Date: Jul. 13, 1995

(30) Foreign Application Priority Data

Jan. 7, 1994 (DE) .......................................... 44 00 255

(51) Int. Cl.⁷ ........................... C07H 21/00; C12P 19/34
(52) U.S. Cl. ...................................... 536/25.4; 435/91.1
(58) Field of Search .......................... 536/25.4; 435/91.1

(56) References Cited

U.S. PATENT DOCUMENTS 5,114,858 A   5/1992   Williams et al. ............ 435/270

FOREIGN PATENT DOCUMENTS

| DE | 9112776 | 10/1991 |
| WO | 92/07863 | 5/1992 |
| WO | 92/00132 | 9/1992 |
| WO | 93/11218 | 10/1993 |

*Primary Examiner*—James O. Wilson
*Assistant Examiner*—Howard V. Owens, Jr.
(74) *Attorney, Agent, or Firm*—Jacobson Holman PLLC

(57) ABSTRACT

A method for the size reduction of high-molecular structures, in particular high-molecular nucleic acid structures, in samples wherein the high-molecular structures to be size-reduced are passed through a means provided with at least one porous layer the pore size of which decreases in the direction of the passage of the structures to be size-reduced through the porous layer.

9 Claims, 3 Drawing Sheets

METHOD FOR THE SIZE REDUCTION OF HIGH-MOLECULAR STRUCTURES

Figure 1:
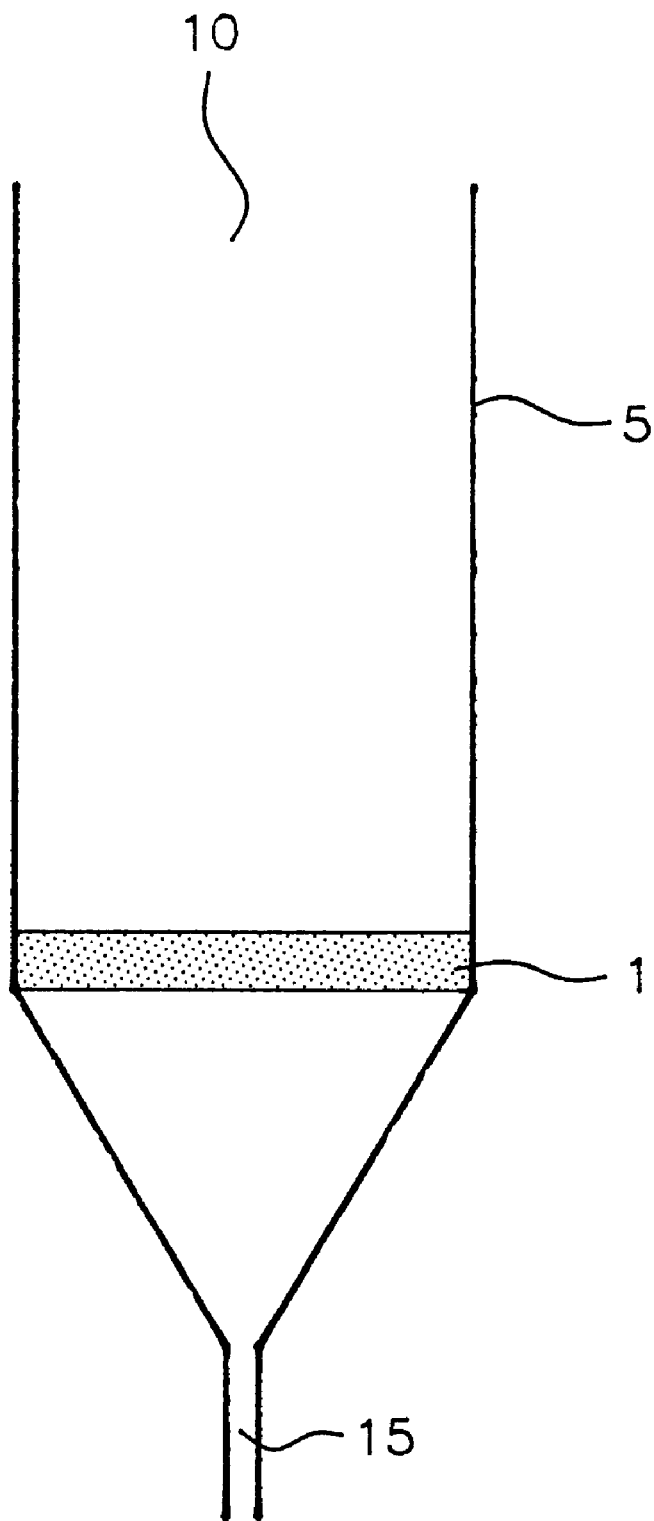

The present invention pertains to a method for the size reduction of high-molecular structures according to claim 1, a device according to claim 7, and uses of the device according to claims 12 to 15.

Many biological isolation methods proceed from cell and tissue lysates, for example, which are frequently highly viscous systems. Due to their high viscosities, such systems can hardly be further processed and are usually subjected to various processes for homogenization or viscosity reduction.

In particular in the isolation of mRNA, it is necessary to homogenize the samples containing these substances in order to obtain non-viscous lysates or solutions. The preparation of homogeneous cell lysates or solutions having low viscosities is necessary in a number of techniques of molecular biology. Some of these techniques will be mentioned in the following for illustrative purposes.

Direct isolation of whole RNA or mRNA from cell or tissue lysates in most cases requires a homogenization step since the hybridization rate between the oligo-dT matrix necessary for mRNA isolation (e.g., cellulose, paramagnetic particles or latex particles) is very low in highly viscous solutions, as opposed to homogeneous solutions. The corresponding matrices may quasi agglomerate with the high-molecular DNA which is also present in the sample and render purification so difficult as even to become impossible in some instances.

Finally, in the preparation of whole RNA, as described, e.g., in German Patent P 43 21 904, the membrane which is necessary for chromatographic purification and is inserted in an apparatus will soon be clotted by highly viscous lysates or solutions.

The protocols for direct mRNA isolations, as known in the prior art using known products, consider that homogenization of the samples containing the substances mentioned is inevitable.

For example, it has been shown that in the polymerase chain reaction (PCR) with genomic DNA better results are achieved if sheared, low molecular weight DNA is employed. This could be related to the fact that smaller DNA fragments are more easily denatured and thus hybridization of the primer (primer annealing) is more efficient. In this connection, it is important that in preparations of nucleic acids (mRNA, whole RNA, and DNA) for PCR, cross contaminations with nucleic acids between samples which are processed simultaneously or succesively and cross contaminations with nucleic acids from other sources are by all means to be avoided since PCR is extremely sensitive so that contaminations with undesired nucleic acids would also be amplified correspondingly.

In the prior art, the following methods are employed essentially for the homogenization or shearing of tissues, cells and/or solutions containing high-molecular substances.

The size reduction (shearing) of high-molecular DNA may be performed by mechanically comminuting a sample deepfrozen in liquid nitrogen by means of mortar and pestle. Also, DNA will be sheared by repeated drawing of the sample containing high-molecular DNA through a cannula into a syringe. In addition to their high expenditure of work, these methods are not capable of ensuring a neat operation. Thus, the homogenization process for the isolation of biomolecules from potentially infectious starting materials, such as human cell and/or tissue samples (biopsy material), is found to be the most dangerous source of contamination of the operator since the homogenizate can squirt over a considerable distance in the conventional homogenization method.

Extraction of nucleic acids and other biomolecules from plant materials is found to be extremely difficult due to the high content of polysaccharides, polyols and/or other secondary metabolites since the substances mentioned form highly viscous lysates or gel-like structures in the commonly employed solutions following lysis of the cells or tissues. Simple centrifugation of the gel-like mass is not successful in most cases since a separation from the solution employed cannot be achieved. The gel-like structures and the high viscosity prevent efficient isolation of nucleic acids or render such isolation altogether impossible in some cases.

For the shearing of high-molecular DNA, there may also be employed specific homogenizers, such as the commercial Ultraturrax, Polytron, Omni, Tissuemizer, and the like. Although this method enables simple and rapid homogenization of virtually any sample, it has a drawback in that specific minigenerators have to be acquired for the homogenization of very small cell, tissue or solution quantities, in particular those which are designated for subsequent analysis by PCR or RT-PCR. In order to avoid cross-contaminations between different cell or tissue samples or other samples in this case, miniaturized disposable generators may also be employed which requires, however, that a relatively expensive device for homogenization is already available. In addition, the miniaturized disposable generators are very costly by themselves.

Another method for homogenization which has proved successful for some applications is ultrasonic treatment of the corresponding sample. In the field mentioned, for example, in PCR applications, this requires expensive equipment. Another drawback is the fact that disposable ultrasonic heads are not available. In addition, there is a risk that the nucleic acids may be too much fragmented by ultrasonic treatment, perhaps until being entirely unsuited for further analysis methods.

DE 41 39 664 A1 pertains to a device and a method for the isolation and purification of nucleic acids. The device for performing the method described consists of a hollow body having an inlet and an outlet wherein a particulate first material based on silica gel is arranged within the hollow body between two fixation means and a second material is arranged between the first material and the outlet, the first and second materials having different adsorption characteristics for nucleic acids.

DE 40 34 036 pertains to a device and a method for the isolation of nucleic acids from cell suspensions. The device for performing this method possesses a cell-uptaking matrix within a hollow body between two porous means. The pore size of said means is larger than the void size of the material forming the matrix.

CLONTECH Labs 1993, "Nucleic Acid Purification with CHROMA SPIN Columns", pertains to a method for the extraction of nucleic acids from agarose gel pieces.

In D. Blöcher and G. Iliakis, Int. J. Radiat. Biol., 1991, vol. 59, 919–926, DNA fragments. are removed from a filter in the course of a non-denaturing filter elution. This appears to involve degradation of DNA fragments at the filter membrane.

Thus, the object of the invention is to provide a method which avoids the drawbacks mentioned of the prior art. A method is to be provided by which efficient preparation of nucleic acids in a simple and cost-saving way without cross-contaminations and, in general, homogenization of viscous systems, can be achieved.

The object of the invention is achieved by a method with the features of claim 1. The subsequent subclaims 2 to 6 pertain to preferred embodiments of the method according to the invention.

Claims 7 to 11 pertain to a device which is particularly suitable for performing the method according to the invention. Claims 12 to 15 pertain to the use of the device according to the invention.

The method according to the invention for the size reduction of high-molecular structures, in particular nucleic acids, starts with charging the system containing the structures to be size-reduced onto a means. Said means includes at least one porous layer which porous layer has an asymmetrical pore size distribution. The pore size decreases in the direction of the passage of the structures to be size-reduced through the porous layer. The term pore size is to be construed as meaning an average pore size. The system containing the high-molecular structures to be size-reduced passes said means, said high-molecular structures being size-reduced during such passage, presumably due to their sensitivity towards mechanical actions. In particular, the system containing the high-molecular structures to be size-reduced may be a system with relatively high viscosity consisting of a cell and/or tissue lysate, or a matrix used for the separation of nucleic acids, such as polyacrylamide gels, or soft tissues (breast tissue, brain, adipose tissue, and the like), or solutions containing high-molecular DNA.

The method according to the invention may also be used to advantage for the homogenization of inhomogeneous viscous systems, in particular cell and tissue lysates, if the means described above has at least two porous layers. The system containing the high-molecular structures to be size-reduced or viscous system to be homogenized passes said means having at least two porous layers wherein the pore size of the porous layer decreases in the direction of the passage of the system to be homogenized. The pore size of the first layer as seen in the direction of the passage may be up to six times the pore size of the underlying second layer. The second layer has a minimum pore size which is essentially determined by the requirement that no clotting of the second layer will occur by the system to be size-reduced or homogenized. Typically, the pore size of the second layer is >10 $\mu$m. This enables the size reduction or homogenization of a matrix as well which has been used for the separation of nucleic acids or proteins, such as polyacrylamide gels.

The process may be repeated any number of times if it is found that a sufficient shearing has not been achieved after one passage. It is understood that the method according to the invention may also be modified by extending the distance to be passed by the structure to be size-reduced by varying the thickness of the porous layer or layers employed.

Cells and/or tissues may optionally be taken up in a buffer containing guanidine thiocyanate or in a buffer containing proteinase K or the like protease and/or optionally be incubated therein. The cells or tissue pieces may have been comminuted first by mechanical action.

The device according to the invention present no difficulties in the isolation of nucleic acids. Highly viscous material is sheared in this device so that the lysate may subsequently be used as such for further processing while cell and tissue residues are removed from the lysate by the filtration effect of the device.

The passage of the viscous system through the pores surprisingly causes shearing of substances which are sensitive towards mechanical influences. In particular high-molecular nucleic acid, such as genomic DNA, is sheared by the passage. At the same time, solutions containing genomic DNA or other high-molecular compounds can be homogenized and high-molecular structures, such as polyacrylamide gels, can be size-reduced by the method according to the invention. After such homogenization, the corresponding samples have a lower viscosity than they had at the beginning of the treatment. Correspondingly, the samples are more easily further processed.

The method according to the invention enables the sample preparation for the isolation of RNA and DNA. Thereby, RNA molecules become available, in particular, in a range of sizes of from 0.8 to 20 kbp. DNA molecules having sizes of from 40,000 to 50,000 bp are obtained from samples containing DNA in the form of chromosomal DNA.

In a preferred embodiment of the method according to the invention, the system containing the high-molecular structure to be size-reduced or the system to be homogenized (sample) is charged onto the means having at least one porous layer and pressed through said at least one porous layer at the sample side by mechanical action. The passage may be effected, for example, by mechanical action on the sample side, such as increased pressure or gravity, such as may be generated by centrifugation. It is also possible, however, to generate reduced pressure at the side opposite to the sample whereby the viscous system to be homogenized, for example, will then pass through the porous layers of the means.

The device according to the invention advantageously allows sample preparation for PCR (polymerase chain reaction). This reaction is used for DNA amplification. In particular when a layer is used having a pore size within the range of from 20 $\mu$m to 70 $\mu$m, the DNA is predominantly obtained at lengths of from 40 to 60 kb, irrespective of whether the DNA is derived directly from cell lysates or from prepurified solutions. Thus, the present invention may be advantageously combined with the method described in German Patent P 43 21 904. A nucleic acid binding matrix, such as glass fiber, is charged onto the porous layer. The DNA present will then be bound to the matrix at high ionic strengths and then sheared (size-reduced) by passing the porous layer(s) upon elution, e.g., with water.

An analogous procedure is to be used in the one-layer embodiment of the method.

FIG. 1 shows a device adapted to the method according to the invention which is also a subject matter of the present invention according to claim 7. The device has an inlet 10 and outlet 15, and a means 1 arranged within the lumen of a hollow body 5. The means 1 consists of a porous layer the pore size of which decreases in the direction of the passage of the structures to be size-reduced through the porous layer. Said porous layer is preferably made of inert materials, such as inorganic or organic substances, in particular glass frit-like materials or polymeric substances such as used for the construction of membrane filters. There may be mentioned, in particular, polyethylene, polypropylene, polystyrene, and other polymeric hydrocarbon materials, of which the porous layer may be made.

Figure 2:
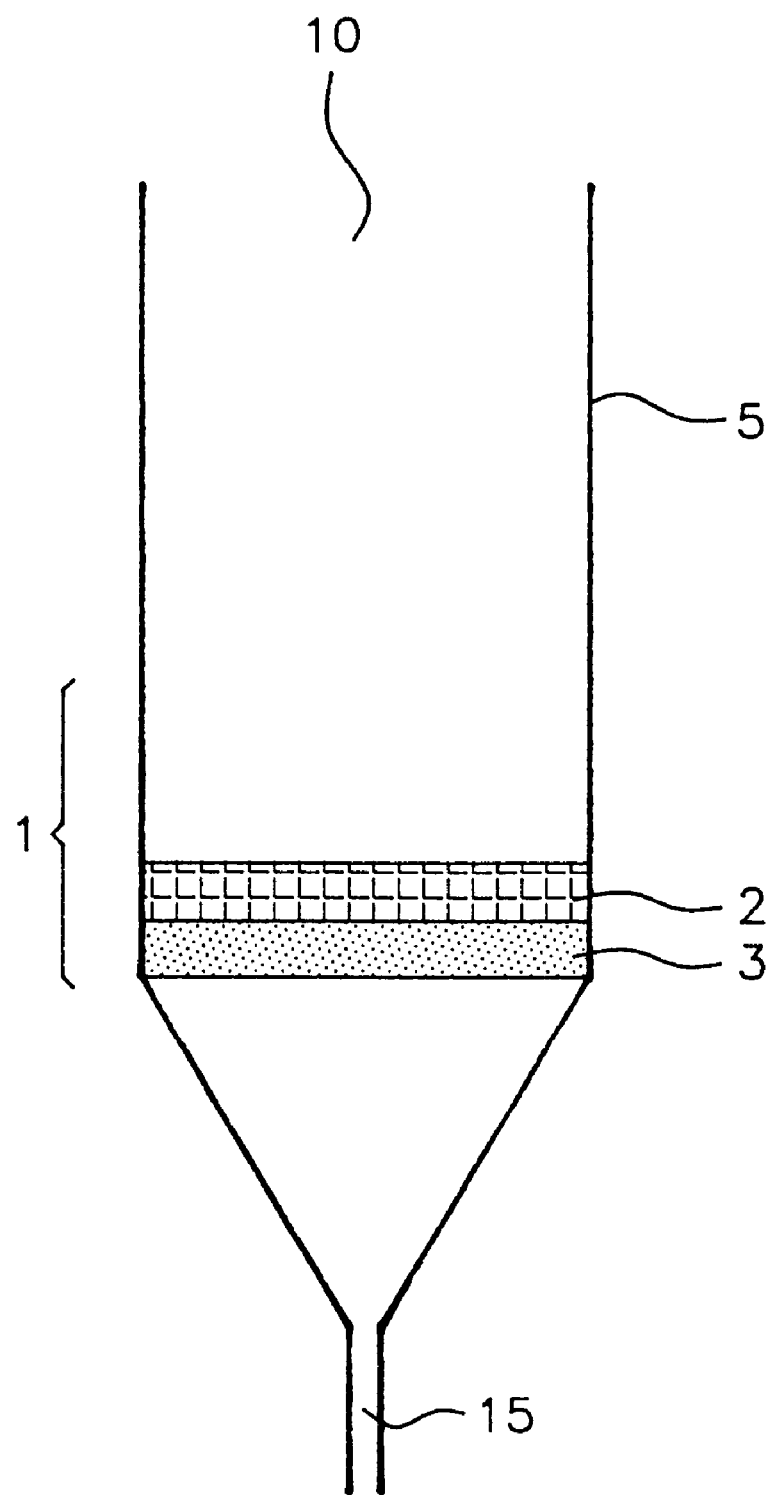

FIG. 2 shows a device adapted to the method according to the invention which is also a subject matter of the present invention according to claim 8. It has an inlet 10 and outlet 15, and a means 1 arranged within the lumen of a hollow body 5. The means 1 consists of at least two layers 2, 3 wherein the pore size of layers 2, 3 decreases in the direction towards outlet 15. The system to be homogenized is homogenized by its passage through layers 2, 3. Preferably, the layers are fixed in the hollow body 5 which, in particular, has a cylindrical shape. Such fixation may be achieved by friction, such as, for example, by jamming in the means 1 with layers 2, 3, or by bonding it to the wall of the hollow body which, in particular, has a cylindrical shape. The layers have pore sizes in the range of from 1 mm to 10 $\mu$m, the respective pore sizes of the layers being graduated.

Figure 3:
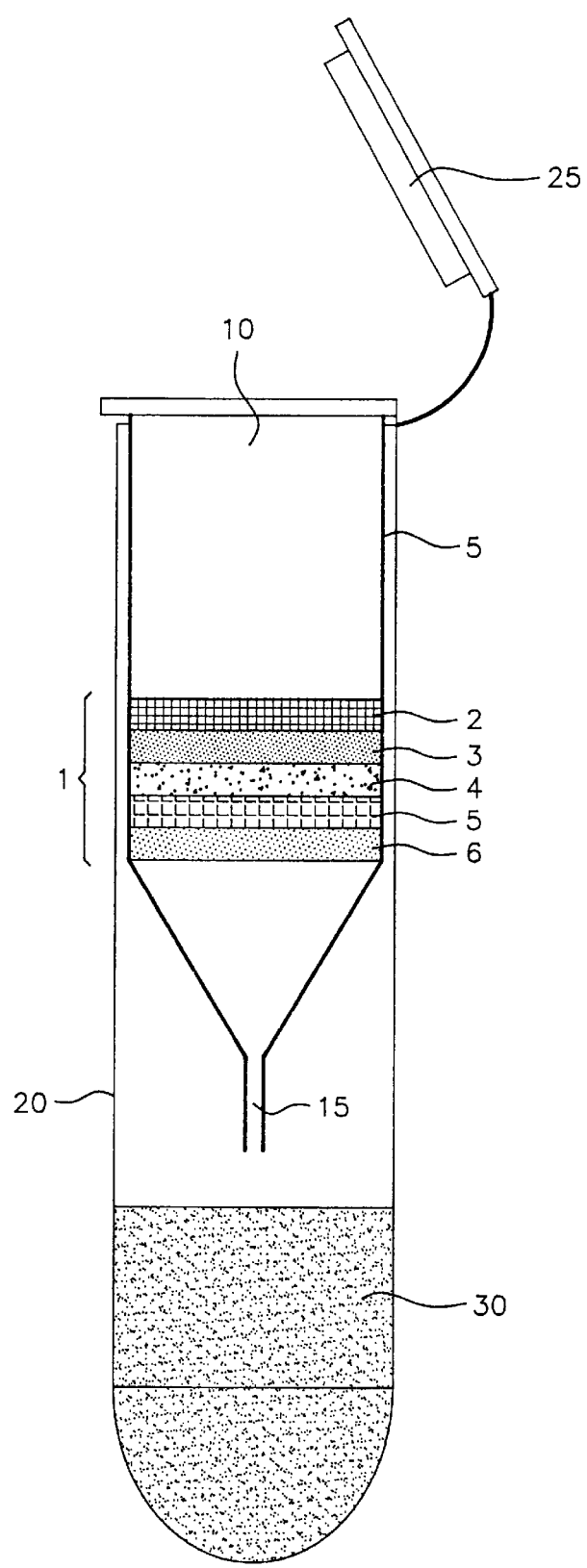

Graduation of the pore sizes of the layers is effected by the first layer 2, as seen in the direction of sample flow, having a pore size which is up to six times that of the second layer 3 the pore size of which is >10 μm. In a special arrangement, the device according to the invention is matched to commercial centrifuge tubes. FIG. 3 shows such an arrangement. A hollow body which essentially cylindrical shape tapering off conically at the outlet 15 is arranged at the upper end of the centrifuge tube in such a manner that the inlet 10 of the device to be employed according to the invention is also arranged at the opening of centrifuge tube 20. The arrangement may be sealed by means of a cap 25 which is arranged either at the device according to the invention or at the centrifuge tube itself. Inside the device according to the invention, five layers 2, 3, 4, 5, 6 are preferably arranged such that surface of the layer having the respectively smaller pore size is immediately adjacent to that of the layer having the larger pore size. After the passage of the viscous system through the means 1, the homogenized solution 30 will gather at the bottom of centrifuge tube 20.

In the arrangement shown in FIG. 3, the porous layers have pore sizes, starting with layer 2, of about 200 μm, about 75 μm (layer 3), about 35 μm (layer 4), about 20 μm (layer 5), and about 10 μm (layer 6). It is understood that the device may also employed having but one porous layer as described above.

Those skilled in the art will understand that a device in a one-layer embodiment which has no multilayer structure is to be considered an equivalent embodiment. In this case, it is important that the device 1 in its one-layer embodiment have a pore size gradient in the direction from one surface of the layer to the opposite surface.

The uses according to the invention of the devices described provide for the homogenization of viscous systems, such as, for example, cell and tissue lysates, in a simple and cost-saving way and conversion thereof to systems of lower viscosities.

It has been shown, surprisingly, that high-molecular nucleic acid is sheared by the passage through the means present in the device to be used according to the invention so that it may be further processed more easily and in a more reproducible manner in the subsequent molecular-biological processing steps. This is true, in particular, with the preparation/purification of genomic DNA, mRNA and whole RNA/DNA. It has further been shown, surprisingly, that high-molecular structures, such as polyacrylamide gels, may be size-reduced in a simple way so that, e.g., nucleic acids and/or proteins may readily be isolated from a separation matrix.

In another further development of the device according to the invention, the means 1 is arranged inside a syringe (as the cylindrical hollow body 5). The viscous system to be homogenized is drawn into the syringe through the cannula and passes through means 1 arranged close to the joint between cannula and syringe. When the sample has been drawn into the syringe, it may pass through means 1 again by pressing it out. This process may be repeated several times, if desired, to ensure sufficient homogenization, in particular of highly viscous solutions containing high-molecular nucleic acids. The layer having the largest pore size may be facing the cannula of the syringe.

By the method according to the invention and/or the device according to the invention, nucleic acids, such as genomic DNA or whole nucleic acids, may advantageously isolated from the corresponding matrices which are commonly employed for the separation of nucleic acids. There may be mentioned, in particular, polyacrylamide gels which are employed as the matrix for gel electrophoretic separations of DNA or RNA. After electrophoresis, the bands in which the nucleic acids of a given size have accumulated are merely separated from the other gel components by punching or cutting and then passed through the device to be used according to the invention, using the method as described according to the invention. It has been shown, surprisingly, that the gel residues present in the homogenized solution do not adversely affect the subsequent molecular-biological nucleic acid processing steps.

Thus, the present invention describes a simple, safe and cost-saving method for the size-reduction and homogenization of viscous systems, in particular cell and tissue lysates or systems containing high-molecular nucleic acids.

The present invention will be explained in more detail by means of the following examples.

EXAMPLES

Compositions of the solutions used in examples 1–3
OL: 4 M guanidine isothiocyanate, 25 mM sodium citrate, pH 7.0, 20 mM EDTA, pH 8.0;
DB: 25 mM sodium citrate, pH 7.0, 0.20 EDTA, pH 8.0, 0.75% sarcosin;
OW: 150 mM NaCl, 1 mM EDTA, pH 8.0, 10 mM Tris-HCl, pH 7.5;
TE: 10 mM Tris-HCl, pH 7.5, 1 mM EDTA, pH 8.0.

Example 1

Homogenization of cell lysates and subsequent direct isolation of poly $A^+$ mRNA from HeLa cells HeLa cells grown on a 10 cm cell culture dish to confluency (about $1 \times 10^7$ cells) were lysed in 600 μm OL directly on the cell culture dish. The lysate was accumulated on one side of the dish by means of a cell scraper and pipetted onto a device according to the present patent application. Inside the device, two layers of CELLPOR PE filter sheets having pore sizes of 200 μm and 35 μm, respectively, were arranged such that the layer having the smaller pore size was facing towards the outlet. The device was placed in a 2 ml microcentrifuge tube. Then, the viscous lysate was centrifuged through the device for 3 min at maximum speed in a conventional table-top centrifuge (about 14,000 to 18,000× g). To the non-viscous lysate thus obtained was added 1200 μm of DB, followed by centrifugation for 3 min. The supernatant was transferred to a new centrifuge tube, to which 35 μl of an Oligotex suspension was added, and incubated for 10 min. Then, the mRNA:Oligotex complexes were pelletized and washed twice in 600 μl of OW by resuspending and centrifuging. Then, the mRNA was eluted from the Oligotex particles in water and transferred to a new microzentrifuge tube as a purified mRNA fraction after centrifugation and pelletization of the latex particles.

Example 2

Enhancement of the amplification efficiency in PCR by shearing of the DNA

Genomic DNA with an average size of 100 kb was isolated from HeLa cells according to the procedure described in "Current Protocols in Molecular Biology" (Ausubel et al., Wiley and Sons, Boston, vol. 1, pages 2.2.1 to 2.2.3). In parallel preparations, the DNA was centrifuged for 2 min in Tris buffer through a device according to the present patent application including one layer each of CELLPOR PE filter sheets having pore sizes of 200 μm, 50 μm, 35 μm, and 5 μm, respectively. Then, in PCR, 1 μg each of the differently sheared DNA as well as unsheared DNA were employed to amplify a 140 bp fragment of the globin gene. In this PCR, at equal numbers of cycles, a higher yield of amplificate was achieved with sheared DNA than with unsheared DNA.

Example 3

Isolation of RNA from a piece of polyacrylamide gel after size-reduction of the polyacrylamide gel In vitro transcribed RNA was applied to a denaturing 5% polyacrylamide/urea gel in order to separate the "full length" transcript from shorter transcripts. After staining the RNA with ethidium bromide, the corresponding band at 360 bp was excised and transferred to a device according to the present patent application having one layer of CELLPOR PE filter sheets of 200 μm pore size. Then, 500 μl of TE buffer was pipetted onto the device. Thereafter, centrifugation was performed for 3 min at maximum speed in a conventional table-top centrifuge (about 14,000 to 18,000× g). The piece of gel thus size-reduced was again transferred to a device having one layer of a CELLPOR PE filter sheet of 1 μm pore size in order to separate the small polyacrylamide/urea gel pieces from the liquid. The aqueous fraction in the collecting vial was then extracted with phenol/chloroform. The aqueous upper phase was pipetted off and the RNA dissolved therein precipitated with LiCl (final concentration 3 M) at 20° C. for 3 hours. The RNA pellet was washed twice with 70% alcohol, centrifuged off and dried in vacuo. Then, the RNA was dissolved in TE.

Example 4

Isolation of RNA from soft tissue following homogenization of the tissue through the device according to the invention Compositions of the solutions used in examples 4 and 5
R1: 3.5 M guanidine isothiocyanate, 25 mM sodium citrate, pH 7.0, 1% β-mercaptoethanol
R2: 900 mM GTC, 25 mM Tris-HCl, pH 7.5, 10% ethanol
TE: 50 mM Tris-HCl, pH 7.5, 80%-ethanol Twenty mg of breast tissue were placed on a device according to the invention and 350 μl of lysing buffer R1 were pipetted thereto. Inside the device, 2 layers of CELLPOR PE filter sheets having pore sizes of 200 μm and 50 μm, respectively, were arranged such that the layer having the smaller pore size was facing towards the outlet. The device was placed in a 2 ml microcentrifuge tube. Then, the viscous lysate was centrifuged through the device for 3 min at maximum speed in a conventional table-top centrifuge (about 14,000 to 18,000× g). To the non-viscous lysate thus obtained was added 350 μl of 70% ethanol, followed by pipetting onto a RNeasy Spin column suspended in a 2 ml microcentrifuge tube according to German Patent P 44 04 361. This was followed by centrifugation at 8000× g for 15 s in a standard table-top centrifuge. The RNeasy Spin column was transferred to a new 2 ml tube and washed with 700 μl of washing buffer R2 (centrifugation at 8000× g for 15 s). Then, the column was similarly washed twice with 500 μl of washing buffer TE. For eluting the RNA, the column was inserted in a new 1.5 ml reaction vessel, 50 μl of DEPC treated water was pipetted directly onto the membrane of the Spin column and the RNA was subsequently collected upon centrifugation at 8000× g for 1 min.

Example 5

Isolation of RNA from plant cells and tissues following centrifugation through the device according to the invention One hundred mg of leaf tissue from pelargoniums was triturated under liquid nitrogen to give a fine powder. Then, the powder was lysed in 450 μl of lysing buffer and the lysate thus obtained pipetted onto the device according to the invention. Inside the device, 2 layers of CELLPOR PE filter sheets having pore sizes of 200 μm and 50 μm, respectively, were arranged such that the layer having the smaller pore size was facing towards the outlet. The device was placed in a 2 ml microcentrifuge tube. Then, the viscous lysate was centrifuged through the device for 3 min at maximum speed in a conventional table-top centrifuge (about 14,000 to 18,000× g). To the non-viscous lysate thus obtained was added 225 μl of 100% ethanol, followed by pipetting onto a RNeasy Spin column suspended in a 2 ml microcentrifuge tube according to German Patent P 44 04 361. This was followed by centrifugation at 8000× g for 15 s in a standard table-top centrifuge. The RNeasy Spin column was transferred to a new 2 ml tube and washed with 700 μl of washing buffer R2 (centrifugation at 8000× g for 15 s). Then, the column was similarly washed twice with 500 μl of washing buffer TE. For eluting the RNA, the column was inserted in a new 1.5 ml reaction vessel, 50 μl of DEPC treated water was pipetted directly onto the membrane of the Spin column and the RNA was subsequently collected upon centrifugation at 8000× g for 1 min.

What is claimed is:

1. A method for isolating nucleic acid structures from a sample, comprising
    passing a sample of polyacrylamide gel through a device, said device including means having at least one porous layer, the pore size of which decreases, in the direction of the passage of the sample through the porous layer, whereby said nucleic acid structures are reduced in size and extracted from other materials in the sample in a resulting filtrate, said filtrate having a viscosity lower than said sample, and
    processing said filtrate having a lower viscosity.

2. The method according to claim 1, wherein said means has at least two layers, of different average pore sizes wherein a first of said layers, as seen in the direction of sample flow, has an average pore size up to six times the pore size of a second of said layers, and the second layer has an average pore size larger than 10 μm.

3. The method according to claim 1, effecting homogenization of the nucleic acid structures.

4. The method according to claim 1, wherein the sample is charged onto the means having at least one porous layer and passed through the layer by mechanical action.

5. The method according to claim 1, wherein said sample contains genomic DNA and wherein said device has an inlet (10) and outlet (15), and at least one of said means arranged within the lumen of a hollow body (11) containing a layer (1) for the size-reduction of the nucleic acid structures, wherein the average pore size of the layer (1) decreases in the direction of the passage of the structures through the porous layer (1), for size reduction of the genomic DNA, homogenization of the genomic DNA, and size-reduction of the polyacrylamide gel.

6. The method according to claim 1, wherein said device has an inlet (10) and outlet (15), and at least one of said means arranged within the lumen of a hollow body (11) containing a layer (1) for the size-reduction of the nucleic acid structures, wherein the average pore size of the layer (1) decreases in the direction of the passage of the nucleic acid structures through the porous layer (1), effecting homogenization of the nucleic acid structures.

7. The method according to claim 1, wherein said sample is a plant or tissue cell lysate containing mRNA and whole RNA, or mRNA, whole RNA, and DNA, and wherein said device has an inlet (10) and outlet (15), and at least one of said means arranged within the lumen of a hollow body (11) containing a layer (1) for the size-reduction of nucleic acid structures, wherein the average pore size of the layer (1) decreases in the direction of the passage of the nucleic acid structures through the porous layer (1).

8. The method of claim 4, wherein the nucleic acids consist of genomic DNA.

9. The method of claim 5, wherein said mechanical action involves increased pressure or increased gravity at the sample side, or reduced pressure at the side opposite to the sample.

* * * * *

UNITED STATES PATENT AND TRADEMARK OFFICE
CERTIFICATE OF CORRECTION

PATENT NO.    : 6,586,585 B1
DATED         : July 1, 2003
INVENTOR(S)   : Helge Bastian It is certified that error appears in the above-identified patent and that said Letters Patent is hereby corrected as shown below:

Title page,
Item [22], PCT Filed, change "Jan. 5, 1996" to -- Jan. 5, 1995 --

Signed and Sealed this

Thirty-first Day of May, 2005

JON W. DUDAS
*Director of the United States Patent and Trademark Office*